US012773265B2

(12) United States Patent
Qian et al.

(10) Patent No.: US 12,773,265 B2
(45) Date of Patent: Oct. 27, 2026

(54) ABLATION LESION DEVICE

(71) Applicants: The University of Sydney, New South Wales (AU); Western Sydney Local Health District, New South Wales (AU)

(72) Inventors: Pierre Qian, New South Wales (AU); Michael Anthony Barry, New South Wales (AU)

(73) Assignees: The University of Sydney, New South Wales (AU); Western Sydney Local Health District, New South Wales (AU)

(*) Notice: Subject to any disclaimer, the term of this patent is extended or adjusted under 35 U.S.C. 154(b) by 807 days.

(21) Appl. No.: 17/142,943

(22) Filed: Jan. 6, 2021

(65) Prior Publication Data

US 2021/0186608 A1 Jun. 24, 2021

Related U.S. Application Data

(63) Continuation of application No. PCT/AU2019/050754, filed on Jul. 18, 2019.

(30) Foreign Application Priority Data

Jul. 19, 2018 (AU) ................................ 2018902618

(51) Int. Cl.
*A61B 18/18* (2006.01)
*A61B 18/00* (2006.01)

(52) U.S. Cl.
CPC *A61B 18/1815* (2013.01); *A61B 2018/00077* (2013.01); *A61B 2018/00083* (2013.01);
(Continued)

(58) Field of Classification Search
None
See application file for complete search history.

(56) References Cited

U.S. PATENT DOCUMENTS 4,920,980 A 5/1990 Jackowski
5,328,471 A * 7/1994 Slepian ............... A61L 24/0031
604/101.03

(Continued)

FOREIGN PATENT DOCUMENTS

AU 2006292698 A1 3/2007
CN 101969875 A 2/2011

(Continued)

OTHER PUBLICATIONS

EP19837309.4, "European Search Report", Mar. 17, 2022, pp. 1-11.

(Continued)

*Primary Examiner* — Joanne M Rodden
*Assistant Examiner* — Nora W Rhodes
(74) *Attorney, Agent, or Firm* — Kilpatrick Townsend & Stockton LLP

(57) ABSTRACT

The invention relates to an ablation device for delivery of microwave energy to a selected region of tissue, in particular for producing deep endocardial or epicardial ventricular lesions, such as for the treatment or prevention of arrhythmias.
The device includes a microwave radiation antenna electrically connectible via a microwave feedline to an electrical microwave system, the microwave antenna configured to generate a microwave field able to ablate tissue in said selected region of tissue, the antenna positioned within an antenna-receiving portion of an elongated catheter configured to allow fluid flow along the catheter to exit through one or more orifices in the catheter wall, the catheter provided with an electrical sensing system including one or more metal electrodes and being independent of the electri-
(Continued)

cal microwave system, the device configured such that in use the electrical sensing system includes an electric circuit which incorporates an ionic conductivity bridge formed between said one or more metal electrodes and the fluid exiting said one or more orifices, the ionic conductivity bridge traversing said catheter antenna-receiving portion.

11 Claims, 6 Drawing Sheets

(52) U.S. Cl.
CPC ............... *A61B 2018/00178* (2013.01); *A61B 2018/00577* (2013.01); *A61B 2018/00744* (2013.01); *A61B 2018/00773* (2013.01); *A61B 2018/183* (2013.01); *A61B 2018/1861* (2013.01)

(56) References Cited

U.S. PATENT DOCUMENTS 5,487,391 A 1/1996 Panescu
5,662,680 A * 9/1997 Desai ................ A61B 18/1477 606/210
6,027,500 A 2/2000 Buckles et al.
6,210,367 B1 4/2001 Carr
6,635,055 B1 10/2003 Cronin
7,566,341 B2 7/2009 Keller et al.
8,382,750 B2 2/2013 Brannan
11,324,408 B2 5/2022 Wang
11,701,158 B2 * 7/2023 Chou .................... A61B 18/00 606/1
2004/0049254 A1 3/2004 Longo
2005/0267463 A1 12/2005 Vanney
2007/0066972 A1 3/2007 Ormsby et al.
2007/0203551 A1 * 8/2007 Cronin .................. A61B 18/04 607/101
2008/0183169 A1 7/2008 Klimovitch et al.
2008/0294041 A1 11/2008 Kassab
2009/0062684 A1 3/2009 Gregersen et al.
2009/0240249 A1 9/2009 Chan et al.
2009/0248006 A1 * 10/2009 Paulus .................. A61B 18/18 607/156
2010/0069921 A1 3/2010 Miller et al.
2010/0198040 A1 8/2010 Friedman et al.
2010/0262137 A1 10/2010 Nye et al.
2011/0040162 A1 2/2011 Kinnison
2011/0082383 A1 4/2011 Cory et al.
2011/0291736 A1 12/2011 Klimovitch et al.
2011/0306867 A1 12/2011 Gopinathan et al.
2012/0116486 A1 5/2012 Naga et al.
2012/0157988 A1 6/2012 Stone et al.
2012/0259326 A1 10/2012 Brannan et al.
2012/0265200 A1 * 10/2012 Curley ................ A61B 18/082 606/41
2013/0226169 A1 8/2013 Miller et al.
2013/0296840 A1 11/2013 Condie et al.
2014/0018788 A1 1/2014 Engelman et al.
2014/0046174 A1 * 2/2014 Ladtkow .............. A61B 5/0036 600/562
2014/0257130 A1 9/2014 Cao et al.
2014/0276743 A1 * 9/2014 Curley ............... A61B 18/1815 606/33
2015/0080875 A1 3/2015 Kasprzyk et al.
2015/0105765 A1 4/2015 Panescu et al.
2015/0267463 A1 9/2015 Yager et al.
2016/0081744 A1 3/2016 Wang
2016/0095535 A1 4/2016 Hettrick et al.
2016/0184008 A1 6/2016 Papaioannou et al.
2016/0199127 A1 7/2016 Prutchi
2016/0242667 A1 8/2016 Fay et al.
2016/0262777 A1 9/2016 Stigall et al.
2017/0095290 A1 4/2017 Sherman et al.
2017/0143414 A1 5/2017 Sliwa et al.
2017/0252101 A1 9/2017 Hata et al.
2017/0306867 A1 10/2017 Zhang
2017/0354364 A1 12/2017 Bar-Tal et al.
2018/0078170 A1 * 3/2018 Panescu ................ A61B 18/00
2018/0125575 A1 5/2018 Schwartz et al.
2018/0289284 A1 10/2018 Panescu et al.
2018/0338703 A1 11/2018 Sulkin et al.
2019/0167147 A1 6/2019 Kassab
2019/0374285 A1 12/2019 Hancock et al.
2020/0375658 A1 12/2020 Qian et al.
2021/0186608 A1 6/2021 Qian et al.
2021/0186609 A1 6/2021 Qian et al.
2021/0196378 A1 7/2021 Qian et al.
2021/0251688 A1 8/2021 Dickhans et al.
2021/0401495 A1 12/2021 Qian et al.

FOREIGN PATENT DOCUMENTS

CN 103096826 A 5/2013
CN 103860266 A 6/2014
CN 105263432 A 1/2016
CN 103096826 B 7/2016
EP 2460486 A1 6/2012
GB 250673 A 4/1926
JP 57187505 U 11/1982
JP 6216755 A 1/1987
JP 08187297 7/1996
JP 2002065693 A 3/2002
JP 2003514635 A 4/2003
JP 2009285463 A 12/2009
JP 2011511424 A 4/2011
JP 2011511538 A 4/2011
JP 2012506300 A 3/2012
JP 2014525814 A 10/2014
JP 2016127919 A 7/2016
JP 2016532497 A 10/2016
JP 2018522612 A 8/2018
JP 2019500170 A 1/2019
JP 2021531841 A 11/2021
WO 9835611 A1 8/1998
WO 1998/049957 11/1998
WO 9956642 A1 11/1999
WO 2000/035363 6/2000
WO 02061880 A2 8/2002
WO 2009094392 A2 7/2009
WO 2009098513 A1 8/2009
WO 2011060200 A1 5/2011
WO 2012058434 A1 5/2012
WO 2014188430 A2 11/2014
WO 2016054379 A1 4/2016
WO 2016090175 A1 6/2016
WO 2016/197206 12/2016
WO 2017056056 A1 4/2017
WO 2017093926 A1 6/2017
WO 2018023132 A1 2/2018
WO 2018027174 A1 2/2018
WO 2018081540 A1 5/2018

OTHER PUBLICATIONS

EP19837309.4, "Extended European Search Report", Jun. 14, 2022, 11 pages.
Chen, et al., "Renal Artery Vasodilation May Be An Indicator of Successful Sympathetic Nerve Damage During Renal Denervation Procedure", Scientific Reports, vol. 6, Nov. 16, 2016, pp. 1-10.
Doltra, et al., "Effects of Renal Denervation on Renal Artery Function in Humans: Preliminary Study", Plos One, vol. 11, No. 3, Mar. 22, 2016, pp. 1-14.
Chen, et al., "Renal Artery Vasodilation May Be An Indicator of Successful Sympathetic Nerve Damage During Renal Denervation Procedure", Scientific Reports, vol. 6, No. 37218, Nov. 16, 2016, pp. 1-10.
JP2020-570811, "Office Action", Apr. 14, 2023, 6 pages.
JP2020572955, "Office Action", May 22, 2023, pp. 1-11.
JP2020-572968, "Japanese Office Action", May 11, 2023, pp. 1-7.
PCT/AU2019/050754, International Search Report, Jan. 23, 2020, pp. 1-11.

(56) References Cited

OTHER PUBLICATIONS

PCT/AU2019/050754, "Written Opinion", Jan. 23, 2020, pp. 1-8.
U.S. Appl. No. 16/994,134, "Non-Final Office Action", Oct. 24, 2023, 7 pages.
U.S. Appl. No. 17/171,878, "Non-Final Office Action", Nov. 21, 2023, 13 pages.
CN202080027495.0, "Office Action", Dec. 26, 2023, 12 pages.
JP2021-549554, "Office Action", Dec. 1, 2023, 11 pages.
201980053897.5, "CN Office Action", Nov. 20, 2023, pp. 1-15.
U.S. Appl. No. 17/171,837, "Non-Final Office Action", Jul. 8, 2024, 10 pages.
U.S. Appl. No. 17/468,420, "Non-Final Office Action", Jun. 6, 2024, 14 pages.
U.S. Appl. No. 17/171,837, "Final Office Action", Feb. 11, 2025, 10 pages.
U.S. Appl. No. 17/468,420 , Non-Final Office Action, Mailed on Nov. 7, 2024, 12 pages.
U.S. Appl. No. 17/171,837, "Non-Final Office Action", May 9, 2025, 10 pages.
U.S. Appl. No. 17/468,420, "Final Office Action", Apr. 18, 2025, 14 pages.
U.S. Appl. No. 17/171,837, "Final Office Action", Nov. 28, 2025, 12 pages.
U.S. Appl. No. 17/468,420, "Non-Final Office Action", Sep. 16, 2025, 14 pages.
U.S. Appl. No. 17/171,837, "Notice of Allowance", Feb. 25. 2026, 7 pages.
U.S. Appl. No. 17/468,420, "Non-Final Office Action", Apr. 6, 2026, 40 pages.

* cited by examiner

ABLATION LESION DEVICE

CROSS-REFERENCES TO RELATED APPLICATIONS

This application claims priority to and is a continuation of International Patent Application No. PCT/AU2019/050754, filed Jul. 18, 2019; which claims priority from AU Patent Application No. 2018902618, filed Jul. 19, 2018. The entire contents of each of the PCT/AU2019/050754 and the AU Patent Application No. 2018902618 are hereby incorporated by reference in their entirety for all purposes.

FIELD OF THE INVENTION

The present invention relates to an ablation lesion device, and in particular such a device for delivery of microwave energy to a selected region of tissue.

BACKGROUND OF THE INVENTION

Approximately 17 million people die each year from cardiovascular disease, with up to a quarter of these being sudden deaths due to ventricular arrhythmias. Ventricular arrhythmias are abnormally rapid heart rhythms that can occur after injury to the main pumping chambers of the heart (the ventricles), most commonly following a heart attack.

Implanted cardiac defibrillators (ICDs) are used to prevent death in high risk patients by monitoring heart rhythm and providing a means to terminate ventricular arrhythmias when they occur. However, ICDs do not prevent arrhythmias and many patients experience recurrent ventricular tachycardia (VT) and device shock, both of which can reduce quality of life and increase mortality. The efficacy of anti-arrhythmic drugs for preventing VT has been generally disappointing.

Radiofrequency ablation using catheters introduced into the heart via the vasculature to identify and target critical portions of VT circuits can be effective. However, the pattern of ventricular scar that causes VT is variable in anatomy, often extending deep into the myocardium and out of reach for conventional radiofrequency catheter ablation. Radiofrequency energy is deposited at the cardiac surface, with heating to deeper layers occurring through thermal conduction. Irrigated radiofrequency ablation using contact force sensing catheters can be used to create thermal lesions in the myocardium, with a maximum depth of around 7 mm. However, this is insufficient to target arrhythmogenic substrates deep within the ventricular muscle, which has a normal thickness of 10-12 mm. Epicardial approaches to ablation have attempted to overcome the limitations in lesion depth by targeting the same substrate from the exterior of the heart. However, epicardial fat significantly attenuates the resistive heating from radiofrequency ablation and the presence of coronary arteries in the epicardium limits the sites where ablation can be safely performed.

Further, attempts to deliver more radiofrequency energy at higher contact forces to generate larger lesions frequently result in tissue overheating beneath the catheter tissue interface region that can lead to steam pops, and this can cause ventricular perforation and systemic embolism. As noted above, radiofrequency ablation provides direct (resistive) heating only to a small volume of myocardium beneath the catheter tissue interface, while lesion growth is driven by thermal conduction from this hot zone. The high tissue temperatures in the heated zone therefore limit lesion dimensions that can be achieved. As a result of these issues, achieving deep ventricular ablation lesions has continued to present a significant challenge in the field of cardiac electrophysiology.

The inventors have determined that endocardial microwave catheter heating can overcome these limitations by providing the ability to directly heat a larger volume of myocardium, in a manner to safely form deeper lesions. Microwave energy applied in the right way can also penetrate epicardial fat, sparing coronary arteries (because of arterial blood flow) and therefore minimising the potential for arterial injury.

An additional application of microwave ventricular ablation is in the debulking of the left ventricular outflow tract in patients with hypertrophic obstructive cardiomyopathy, whereby the subaortic valve septal myocardium is hypertrophied and obstructs blood flow. Current treatment options for this condition are limited to open cardiac surgery and myotomy or alcohol septal ablation. The latter involves infusion of alcohol via a septal branch of the left anterior descending coronary artery to create a zone of septal infarction with the aim of reducing the muscle bulk at this site. The limitations of this approach include an unpredictable zone of infarction which is governed by vascular territory, risk of high degree atrioventricular block requiring pacemaker implantation, and the creation of ragged zones of tissue injury that can lead to ventricular arrhythmias.

Microwave endocardial ablation for septal reduction can potentially obviate the need for surgery and produce a more predictable and safer septal lesion, thus minimising potential outflow tract obstruction. The phenomenon of sub-endocardial sparing with microwave ablation can potentially spare the myocardial conduction system from injury and reduce the likelihood of requiring pacemaker implantation.

Known endovascular microwave cardiac ablation catheters which include an electrical sensing function employ the ablation electrode as the sensing electrode (or use a sensing electrode electrically coupled to the ablation electrode). This affords less than optimal microwave emission and can cause overheating of the catheter tip, due to a need to maintain physical and electrical contact between the microwave antenna and the target tissue, thus reducing heat dissipation from the catheter tip and increasing resistive heating. At least partly for this reason, microwave cardiac ablation catheters have made little headway over the last 20 years or so in taking the place of RF ablation catheters.

Published patent application WO 2016/197206 (the entire content of which is included herein by reference), to the applicants of the present application, describes a microwave ablation device for renal artery denervation procedures. This device allows ablation of renal nerves without significant damage to the muscular arterial wall and endothelial layers. The device features a microwave radiator encased within an outer sheath, the radiator coupled to a source of microwave energy by way of a shielded line such as a coaxial cable. The sheath allows flow of an irrigation fluid such as a saline solution, which assists with removing localised heat caused by microwave energy radiation. The outer sheath includes locating formations such as radially expanding portions, to aid centring of the device. Whilst this device has proved effective in endovascular denervation, it is not ideally suited to creating deep lesions, nor for cardiac ablation procedures.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

BRIEF SUMMARY OF THE INVENTION

In a first aspect, the invention provides an ablation lesion device for delivery of microwave energy to a selected region of tissue, the device including a microwave radiation antenna electrically connectible via a microwave feedline to an electrical microwave system, the microwave antenna configured to generate a microwave field able to ablate tissue in said selected region of tissue, the antenna positioned within an antenna-receiving portion of an elongated catheter configured to allow fluid flow along the catheter to exit through one or more orifices in the catheter wall, the catheter provided with an electrical sensing system including one or more metal electrodes and being independent of the electrical microwave system, the device configured such that in use the electrical sensing system includes an electric circuit which incorporates an ionic conductivity bridge formed between said one or more metal electrodes and the fluid exiting said one or more orifices, the ionic conductivity bridge traversing said catheter antenna-receiving portion.

In a further aspect, the invention provides an ablation lesion device for delivery of microwave energy to a selected region of tissue, the device comprising:

a microwave radiation antenna electrically connectible via a microwave feedline to a source of microwave energy, the microwave antenna configured to generate a microwave field able to ablate tissue in said selected region of tissue;

a hollow catheter of elongated form extending from a proximal portion to a distal portion including a tip, the catheter having an outer wall to separate an inside and an outside of the catheter;

the catheter including an antenna-receiving part in said distal portion, the catheter configured to provide a passage for said antenna feedline to said antenna-receiving part;

the catheter having a septated form including a first and a second lumen arranged for fluid flow to the catheter distal portion;

said first and second lumens connecting respectively with a first and a second orifice through the catheter outer wall in said catheter distal portion to provide a fluid outflow path from each lumen to the outside of the catheter, the first and second orifices separated in said antenna-receiving part;

at least one of said first and second lumens including an electrode located in the catheter distal portion substantially proximal of said antenna-receiving part.

The catheter device therefore provides an elongated sheath to accommodate the microwave feedline from the proximal end to the antenna in the antenna-receiving part at the tip end of the catheter distal portion, with irrigating, electrically conductive fluid flow (such as saline flow) passing along the first and second lumens and out of the catheter via said first and second orifices. The electrode is connected via an electric lead to a sensing system, to create an electric circuit with a return electrode in order to sense electrical property or activity in or local to said selected region of tissue to allow monitoring of said electrical property or activity during a microwave ablation procedure, the electrical circuit made via the irrigating fluid from the lumen and through the orifice connecting that lumen with the outside of the catheter. In this way, neither the electrode nor the electric lead is positioned substantially within the microwave field.

It will be understood that the term electrode used above refers in general to a metal electrode, use of the invention with a suitable fluid giving rise to a 'virtual sensing electrode' at a position determined by the fluid outflow path and the local tissue where the device is applied. In other words, the electrical connection with the outside of the catheter is by way of the fluid flow.

The first and second orifices are preferably longitudinally separated along said antenna-receiving part, alternatively or additionally they may be separated in the antenna-receiving part in a direction transverse to the longitudinal direction of the catheter Preferably, the first and second lumens respectively include a first and second electrode each located in the catheter distal portion substantially proximal of said antenna-receiving part.

In this way, said electrode and said return electrode are provided by said first and second electrodes, each of which, connected via a respective electric lead to the sensing system, forms part of said electric circuit, the electric circuit made via the irrigating fluid from both the first and the second lumens and through the first and second orifices connecting the respective lumens with the outside of the catheter.

The first and second lumens have no fluid interconnection in the catheter distal portion, so avoiding electrical conduction between them by virtue of the fluid flow inside the catheter.

In other words, the septated form of the catheter provides a substantially higher impedance electrical path between the first and second electrodes inside the catheter than that provided between the first and second orifices outside the catheter, which results in the electric circuit forming via the first and second orifices. This results in the sensed electrical potential approximating that which would be derived from direct sensing electrode measurement between the first and second orifices.

In a preferred form, the catheter distal portion is provided with:

at least one tip orifice in the catheter wall at or close to the tip, and a lumen orifice in the catheter wall proximal of the catheter tip;

said first lumen connecting to said antenna receiving part of the catheter to provide fluid thereto, the fluid exiting the catheter via said at least one tip orifice;

said second lumen terminating in a fluid connection with the outside of the catheter via the lumen orifice;

wherein the at least one tip orifice and the lumen orifice are longitudinally separated along a substantial part of the antenna-receiving part of the catheter;

wherein a first insulated electrical wire is arranged along said first lumen terminating in said first electrode and a second insulated electric wire is arranged along said second lumen terminating in said second electrode.

In this embodiment, the at least one tip orifice provides said first orifice and the lumen orifice provides said second orifice. Hence, the electrical circuit is formed between the first and second electrodes through the irrigation fluid and via the at least one tip orifice and the lumen orifice.

Preferably, the device includes multiple second lumens, each having an electrode and each having a lumen orifice, the lumen orifices substantially longitudinally coincident. Preferably, lumen orifices are substantially longitudinally coincident with the region of maximum microwave field strength.

Preferably, the device includes multiple first lumens, at least one provided with an electrode, all connecting to the antenna-receiving part of the catheter.

In one embodiment, there are at least three of said first lumens and at least three of said second lumens, arranged in an alternating disposition within the catheter in the volume between said microwave feedline and said catheter wall.

Preferably, the antenna is configured to generate the microwave field external of said catheter, the microwave field having a field longitudinal extent which includes the lumen orifices. The lumen orifices are preferably positioned approximately centrally of said field longitudinal extent. During an ablation procedure this assists a user to position the catheter over the targeted region based on sensed electrical cardiac activation information.

In one embodiment, the first and second lumens are connected for common fluid flow in said catheter proximal of said distal portion.

In such an embodiment, the interconnection is sufficiently remote from the location of the first and second electrodes such that when supplied with irrigation fluid a high impedance circuit is created therebetween. Preferably, the interconnection is at least 300 mm from the longitudinal position of the first and/or the second electrode, for example at the proximal end of the catheter.

In use of the device of the invention, the catheter proximal portion is connected to an irrigation fluid system to provide fluid to said first and second lumens.

Preferably, said microwave feedline is arranged along a feedline passage within the catheter separate from said first and second lumens.

The microwave radiation antenna is preferably insulated from fluid flow in said catheter antenna-receiving portion, e.g. by encasing in a suitable polymer.

The invention therefore relates to a method and apparatus for applying microwave energy to tissue, in particular to cardiac tissue, using an irrigated tip ablation catheter adapted for insertion to the locality of a target tissue structure, to create lesions in particular regions such as regions of diseased tissue. The invention includes the use of a lumen structure in the catheter providing irrigation fluid passages to provide flow paths for cooling fluid such as saline solution, as well as a system of one or more virtual sensing electrodes provided by way of saline bridges between electrical conductors and points in the saline flow paths, these points provided by orifices in an external wall of the catheter such as an outer sheath.

As explained above, the invention arises from the inventors' realisation that, where epicardial ventricular ablation may be required to reach arrthymogenic substrate inaccessible from the endocardium, known techniques of radiofrequency energy delivery are limited by epicardial fat and coronary anatomy, rendering such solutions often impractical. Indeed, the current consensus among cardiac electrophysiologists is to avoid radiofrequency ablation within 5 mm of the coronary artery, due to the potential for coronary injury. In contrast, the use of a specially designed microwave catheter device can produce significantly enhanced outcomes, microwave ablation being able to form deep lesions through epicardial fat without acute injury to nearby coronary vessels and lung tissue.

In one form, then, the invention consists of an insulated microwave-emitting unbalanced monopolar catheter. Whilst in certain features this bears some similarity to the device described in WO 2016/197206, rather than a centring mechanism, it employs an outer sheath encasing the radiating element, and includes perforations at the distal end of the catheter to enable (1) open irrigation (including cooling function) and (2) an electrical sensing function.

For use for ventricular arrhythmia ablation, the catheter of the device of the invention has saline electrodes provided by the perforations, the perforations thus functioning both to allow cooling fluid flow to the catheter tip and to enable sensing of local cardiac electrical activity. With the arrangement of the invention a fully insulated antenna and a separate electrical sensing system are provided, with no substantial interaction between the sensing circuit and the local microwave field. This segregation of the ablation and sensing function minimises the risk of the electrodes acting as focal points of heating to the adjacent myocardium and reduces ohmic heating at the microwave antenna or in any electrically contiguous tissue, and prevents the electrodes from shielding the antenna in any way.

As noted above, previous microwave catheter devices used or proposed for cardiac ablation involved the use of cap choke catheters, in which the antenna cap functioned also as the sensing electrode (and hence was not insulated from the endocardial environment). This resulted in a system in which the antenna cap would heat local tissue rapidly and would not deliver lesions significantly deeper than possible with radiofrequency ablation catheters. In contrast, the present invention does not use a part of the catheter that is electrically continuous with the radiating element for sensing of cardiac electrical signals. This enables the insulated antenna to provide significantly better radiant myocardial heating while avoiding ohmic antenna heating, by employing an electrically separately set of electrodes for sensing of cardiac electrical signals.

The invention has application to both endocardial and epicardial ablation, for example it may be used for ventricular arrhythmia ablation (endocardially or epicardially) or hypertrophic cardiomyopathy septal reduction procedures (an endocardial procedure).

The invention thus provides a clinical transcatheter method of creating deep ventricular ablation lesions. In contrast to percutaneous radiofrequency ablation, which has generally remained the only accepted method for ventricular ablation (despite its limited lesion-forming ability), as noted hereinbefore the use of microwave energy is markedly better suited to deep ventricular ablations and potentially safer for use in epicardial ablation.

Particular facets of at least some embodiments of the present invention include the following:

1. An unbalanced monopolar antenna, insulated from the surrounding environment.
2. A separate system of sensing electrodes independent and electrically isolated from the antenna element.
3. The sensing electrodes are formed by insulated wires that run along the coaxial sheath, terminating in electrodes near the junction of the antenna segment and the coaxial cable feedline, electrically continuous with saline lumens connecting to perforations. Irrigated fluid is directed through these saline lumens to exit from the perforations, the fluid at these points functioning as a sensing electrode (with appropriate filtering to remove microwave noise). In this fashion, no metal is introduced into the microwave field, enabling simultaneous sensing of cardiac electrical potentials during ablation while retaining the desired ablation heating pattern.

The invention therefore provides the capacity to form deep endocardial or epicardial ventricular ablation, including through epicardial fat and near coronary arteries.

Preferably, particularly when provided for use in cardiac ablation procedures, the catheter is deflectable, and includes a thermal feedback mechanism such as a thermocouple, for example a thermocouple positioned within 1 mm of the distal end of the microwave feedline.

BRIEF DESCRIPTION OF THE DRAWINGS

Further aspects of the present invention and further embodiments of the aspects described in the preceding paragraphs will become apparent from the following description, given by way of example and with reference to the accompanying drawings.

DETAILED DESCRIPTION OF THE INVENTION

It will be understood that the invention disclosed and defined in this specification extends to all alternative combinations of two or more of the individual features mentioned or evident from the text or drawings. All of these different combinations constitute various alternative aspects of the invention.

Figure 1:
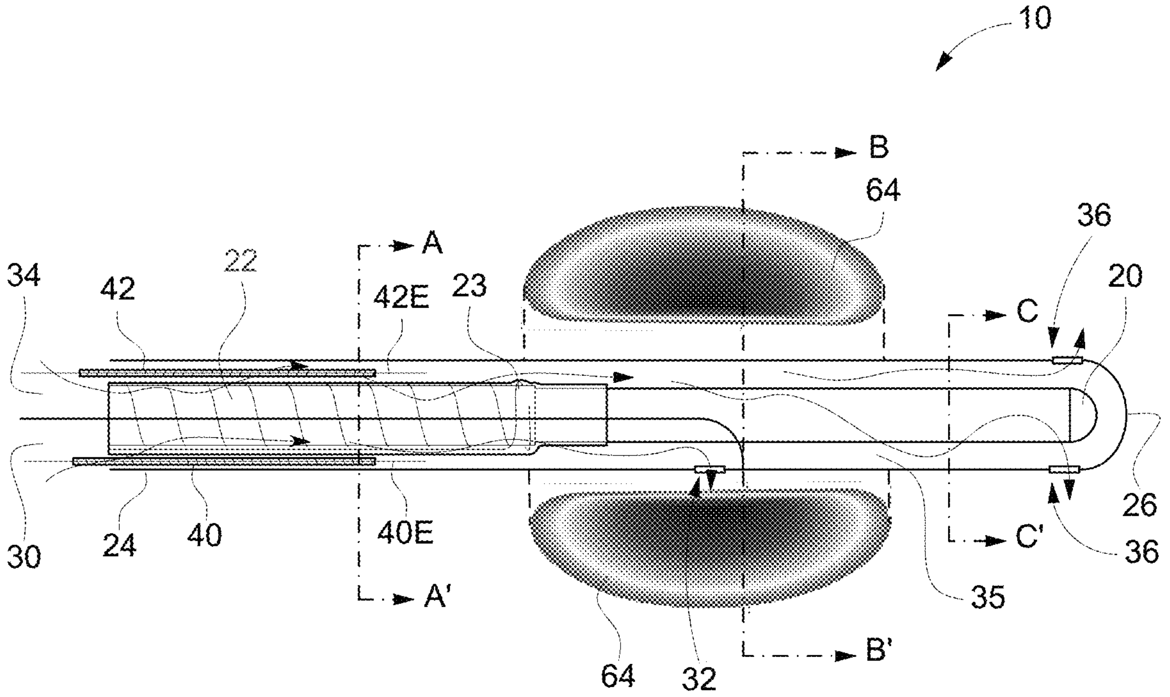
FIG. 1 shows in longitudinal cross sectional view the distal portion of an ablation lesion device in accordance with the present invention.

The diagrammatic illustration provided by FIG. 1 shows a microwave ablation catheter 10 having an elongated, insulated microwave antenna 20 (discussed further below) configured to radiate microwave energy to the surrounding environment. Antenna 20 is electrically coupled to a source of microwave energy (see FIG. 4), preferably a tunable microwave generator, by way of a shielded conductor, namely a coaxial cable 22 having a conductive central core surrounded by a tubular insulating layer, in turn surrounded by a braided outer conductor, wrapped in an insulating outer layer 23. In a form tested by the inventors, antenna 20 is provided by a selected terminal length of the central core of coaxial cable 22, with the outer insulation and braid stripped away over this length. Other components (including optional components) of the microwave antenna and conductor feedline are discussed in publication WO 2016/197206.

It is to be noted that the accompanying drawings are not shown to scale. In FIG. 1, for example, the vertical (width) dimensions are shown at approximately twice the scale of the horizontal (length) dimensions.

Figure 2:
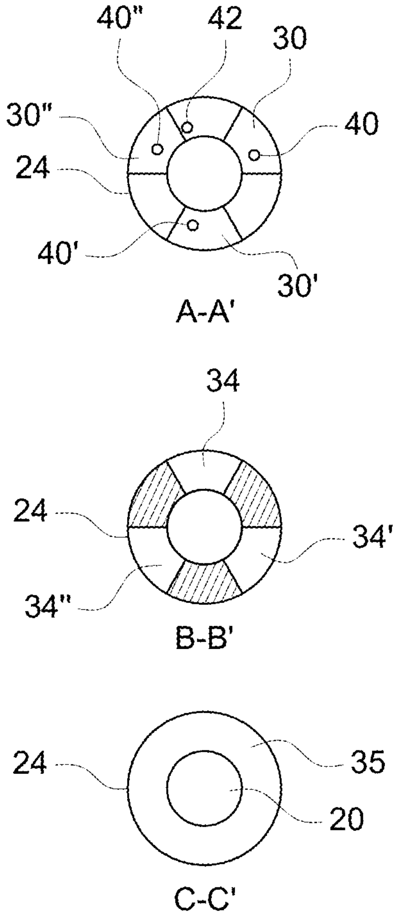
FIG. 2 illustrates three cross sectional views A-A, B-B, C-C of the device of FIG. 1.

Antenna 20 and cable 22 are contained within outer tubular insulating sheath 24, closed at a tip 26 at its distal end. As shown most clearly in the sectional views A-A' and B-B' of FIG. 2, catheter 10 incorporates internal dividing walls connecting to sheath 24 to separate the interior into six elongated lumens. Three of these lumens, 30, 30', 30" form fluid channels which run along sheath 24, terminating in connections to the exterior of sheath 24 by way of orifices 32, 32', 32" respectively (only orifice 32 shown in FIG. 1). Viewed in cross section, these three fluid lumens are regularly angularly spaced around the annular volume between the cable core and the inner surface of sheath 24, each occupying a sector of approximately 60°. It will be understood that these three lumens thus provide mutually separate fluid channels.

In this embodiment, antenna 20 is aligned substantially centrally relative to the longitudinal axis of the catheter sheath 24. However it may be aligned off centre, closer to a first side than an opposite second side, if required to be directional. In this case, the first side of the distal end of catheter 10 is positioned adjacent the target tissue area 62, with microwave energy absorption by the greater volume of fluid in the interior of the catheter between the antenna and the second side.

Catheter 10 is flexible, but substantially non-compressible along its length, to assist insertion and to minimise changes in impedance or fluid flow caused by external compression. Additionally, catheter 10 is formed with relatively high torsional stiffness, such that rotation of the proximal part will translate to corresponding rotation of the distal part. Further, catheter 10 may include one or more guide wires or puller wires to provide directional capability, in order to assist guidance of the catheter tip to the required location and its orientation when in position.

Orifices 32, 32', 32" are axially coincident, at a position corresponding approximately to the centre of the ablation region, as discussed further below. For reasons of clarity the side view of FIG. 3 omits channels 30', 31' and orifices 32', 32", as well as the antenna assembly.

The other three lumens 34, 34', 34" occupy the remaining part of the annular volume between the cable core and the inner surface of sheath 24, and are open ended to coalesce into a common chamber 35 at the distal termination of lumens 30, 30', 30". Chamber 35 thus provides an antenna-receiving region as well as a fluid flow volume, the fluid able to flow freely in the annular volume around antenna 20. Lumens 34, 34', 34" can thus be seen as 'common lumens'. Close to distal end 26 are formed a number of perforations 36 (ideally, three or four) in sheath 24, providing fluid transfer paths from the interior to the exterior, ie. from chamber 35 to the outside.

Figure 3:
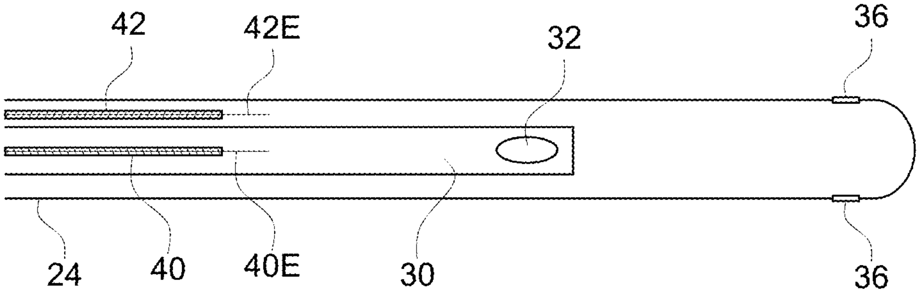
FIG. 3 shows a side view of the device of FIG. 1.

Metal wire conductors are disposed in four of the channels, three wires (40, 40', 40') disposed in the individual lumens 30, 30', 30" respectively, and one wire 42 disposed in one of the common lumens 34, 34', 34". Each wire is insulated along its length save for an uninsulated part at its distal end forming an electrode (respectively 40E and 42E), as shown in FIGS. 1 and 3. Electrodes 40E and 42E may be formed on or attached to the end of the wire conductors, or may be provided simply by exposing a short length of each wire by stripping the insulation.

As shown in FIGS. 1 and 3, the four wires run along the catheter within their respective channels, terminating approximately 20 mm proximal of the braid end (the transition between the shielded feedline cable 22 and antenna 20). As discussed below, this avoids any part of the wires being within the microwave field generated by antenna 20.

Due to the septated structure of the catheter forming the channels, it is impractical to have the E2 saline bridges originate from a common wire, so a wire is run down each of the three channels.

In order to sense the local electrogram of nearby myocardium, known ablation catheters incorporate sensing electrodes at the tip (E1, distal electrode) and at a relatively proximal position along the catheter the shank (E2, second electrode), commonly provided as a ring electrode. These E1 and E2 electrodes are generally separated by a longitudinal distance of 2-10 mm and together afford sensing of a bipolar signal to monitor the effectiveness of the ablation procedure. As the region of ablation increases, the tissue around the catheter tip becomes increasingly electrically inactive, this diminution of the local electrogram providing a key metric to indicate ablation progress.

However, in contrast to such conventional ablation catheters, the device described generates a microwave ablation field which radiates proximal to the catheter tip. Because of this microwave field, sensing wires cannot be run to tip electrodes, as the wires would need to pass through the microwave field region. This would have the effect of shaping the radiation field (thus undesirably affecting the ablation pattern), while the field would interfere with the conductors of the electrocardiogram system. The field therefore makes it impractical to use metal electrodes for sensing myocardial electrograms within the field region, or anywhere close to the field region. Instead, the device of the present invention utilises saline bridges for these electrodes, effectively providing one or more virtual electrodes at or close to one or more of the orifices in sheath 24, at the closest fluid outflow point or points where fluid meets the myocardia. In this way, with the sheath filled with saline solution, the wires are electrically contiguous with the outlet orifices, resulting in a saline bridge being formed between the wire electrodes 40E and the fluid outflow points from orifices 32, 32', 32" (or, more accurately, the points where that fluid outflow meets the myocardium). Similarly, a saline bridge forms between wire electrode 42E and the fluid outflow points from one or more orifices 36.

As will be understood, these saline bridges run through the microwave field region but are not affected by the field. The saline flow (represented by the flow arrows shown in FIG. 1) is necessary for cooling the catheter in operation, and provides a region near to the microwave radiator in which the dielectric constant is high (to help set the effective length of the radiator). The virtual electrode provided by the fluid outflow points from orifices 32, 32', 32" can therefore be seen as functionally equivalent to the E2 sensing electrode of the conventional catheter, while the virtual electrode provided by the fluid outflow points from one or more of orifices 36 can be seen as functionally equivalent to the E1 tip sensing electrode of the conventional catheter. For convenience, the E1/E2 terminology is used below to refer to the respective virtual electrodes of the present invention.

It will be appreciated that unlike the conventional catheter, ablation occurs around the E2 sensing electrode (region of highest microwave field) rather than around the E1 distal electrode. The distal electrode acts as a local 'ground', subtraction from the E2 signal resulting in removal of field noise or other common electrical activation.

As explained above, the saline fluid, in addition to its cooling function, therefore acts as a saline virtual electrode at the point where the fluid outflow from the respective orifice passes into the blood and on to the local myocardium, producing an effective point of contact between the electrogram sensing circuit and the tissue. Trials by the inventors have shown that a 'virtual' saline electrode of this sort performs well, even when placed right in the centre of the field.

As will be understood, although in this embodiment the electrical sensing system uses only a single wire 42 (to provide the E1 electrode), two or three wires may run through respective ones of the common lumens 34, 34', 34".

Further, whilst employing only a single wire 40 in a single lumen 30 is contemplated, the inventors have determined this to be impractical in many situations, as it is then necessary to position and orientate the catheter tip such that the outflow orifice from that lumen is in sufficiently close contact with the myocardium. The inventors have determined that it is therefore highly advantageous to use multiple lumens with multiple wires, with three (as illustrated) or four lumens/wires seen as ideal.

As the skilled reader will understand, with the design of the invention, the sensing electrode is electrically independent of the radiating antenna, being composed of a high loss conductive material (preferably saline) and thus minimising interaction with the microwave field. Further, the design provides effective circumferential cooling of the microwave antenna and ensures that it is not in contact with the cardiac tissue. Hence the device of the invention is capable of cardiac electrogram sensing as well as ablation, without the risks of local tissue heating associated with prior approaches.

As will be understood, whilst lumens 30, 30', 30" terminate and exit the catheter upstream of the catheter tip, orifices 36 are positioned very close to the tip, in order to avoid regions of relatively stagnant fluid which could prevent effective dissipation of heat. In the design illustrated, the fluid completely circulates through chamber 35 including the region adjacent the catheter tip, so precluding the formation of any stagnant zone.

Further, as illustrated in FIG. 1, in the longitudinal direction of the catheter the proximal virtual electrodes are located approximately at the microwave field centre, allowing the physician to line up the catheter and to use the sensed electrocardiogram signals at that point to monitor the ablation operation. As will be understood, the spacing between the virtual electrodes (approximating to the longitudinal spacing between the orifices) is preferably at least half of the length of the lesion to be formed, so that the distal virtual electrode is in unaffected tissue, so best to monitor the electrocardiogram function change during ablation. In common with known ablation catheters using electrical sensing electrodes, suitable spacing for the virtual electrodes is in the range 2-15 mm, depending on the particular application (selected depending on the antenna dimensions and field pattern required).

In a variant, the microwave radiation pattern may be focused closer to the catheter tip (by use of a suitable design and positioning of the antenna), in which case the electrode arrangement could be reversed. Hence the ablation lesion would be formed substantially in line with the catheter tip, with one or more tip flow orifices at a position corresponding to that ablation zone and the other flow orifices (corresponding to the return virtual sensing electrodes) at a position proximal thereto.

The arrangement of the fluid passages and sensing electrodes around the catheter antenna has the effect of:

1) improving microwave radiation due to reduced loss of energy into surrounding medium;
2) limiting catheter-tissue interface heating, by eliminating resistive heating and using the moving columns of saline to absorb and dissipate dielectric heating around the catheter antenna;
3) enabling sensing of electrical activity of cardiac muscle while delivering ablation.

It should also be noted that the presence of saline in close proximity to the antenna is necessary to configure the antenna to radiate in accordance with its length. In other words, a longer antenna would be necessary if the fluid were further from the antenna.

Antenna 20 is insulated from the irrigation fluid that surrounds it by a suitable encapsulation, such as a Teflon tube with an epoxy end cap. The coaxial cable 22 is similarly insulated by a layer of thin heat shrink (such as Palladium™ thermoplastic elastomer). As will be understood, allowing the microwave electrode or the feedline braid to contact the irrigation fluid can impact on the ablation field pattern, and can result in interference with the electrocardiogram system through electrical coupling.

The shape of the lesion delivered by the device of the invention can be modified by changing the antenna length and the degree of antenna balance. For VT ablation, long lesions can be advantageous, particularly if orientated in a selected way. For hypertrophic cardiomyopathy an ideal lesion shape may be broad and long, as the physician will aim to shrink down a relatively large area of muscle in the basal septum. For many applications, however, a generally part-spherical lesion shaping is preferred.

The arrangement of electrodes allows sensing of electrical signals to be done in either a bipolar manner (between each functional E1 electrode and each functional E2 electrode) or in a unipolar manner (from each functional E2 electrode to a common patient return electrode). In the latter technique, the patient electrode may be placed in any suitable location out of the heart but in the blood system (for example, on a separate catheter, or at a separate location on the outside of catheter sheath 24 positioned outside of the heart) or may be provided in a patient return patch placed on the patient's thigh, buttock or back as selected to be appropriate. Whilst the unipolar approach has some applications, it is not preferred for the majority of ablation applications, as the signals generally do not provide sufficient information to monitor success of the procedure. The bipolar approach enables localised electrocardiogram monitoring while excluding far-field signals.

As discussed above, the sensing circuit is realised between the virtual electrodes provided respectively by one or more proximal orifices 32 and one or more distal orifices 36. Additional or alternatively it is possible to realise bipolar electrogram monitoring between two of the orifices 32 (e.g. between wire 40 and 40'). For example, the electrocardiogram monitoring may involve generating a signal representing the vector sum of two different sensing circuits. In this variant the invention could thus be realised using virtual electrodes radially separated (but not necessarily longitudinally spaced) along the catheter. Such an arrangement would provide a closely spaced bipole, whereby the sensed electrical signal is derived from a small region of myocardium substantially between the electrodes, excluding the much larger signal representing the far-field composite of all depolarisations within the heart. The effectiveness of such an arrangement would depend on the orientation of tissue around the electrode orifices, and thus the particular placement of the catheter.

As an example of using multiple sensing circuits, the illustrated embodiment with 6 lumens could employ three combinations of closely-laterally-spaced saline electrode pairs to be used for bipolar electrograms at the site of maximal radiation, as well as one or more more widely spaced electrode pairs along the longitudinal axis of the catheter, thus providing the potential for orthogonal impedance measurement to be made. Whilst (as noted above) the closely spaced bipolar electrogram can be useful to clinically to detect very fine and local activity in a lesion, the orthogonal nature of the sensing may be useful to produce a signal with characteristics more invariant to the wavefront direction of myocardial activation.

Figure 4:
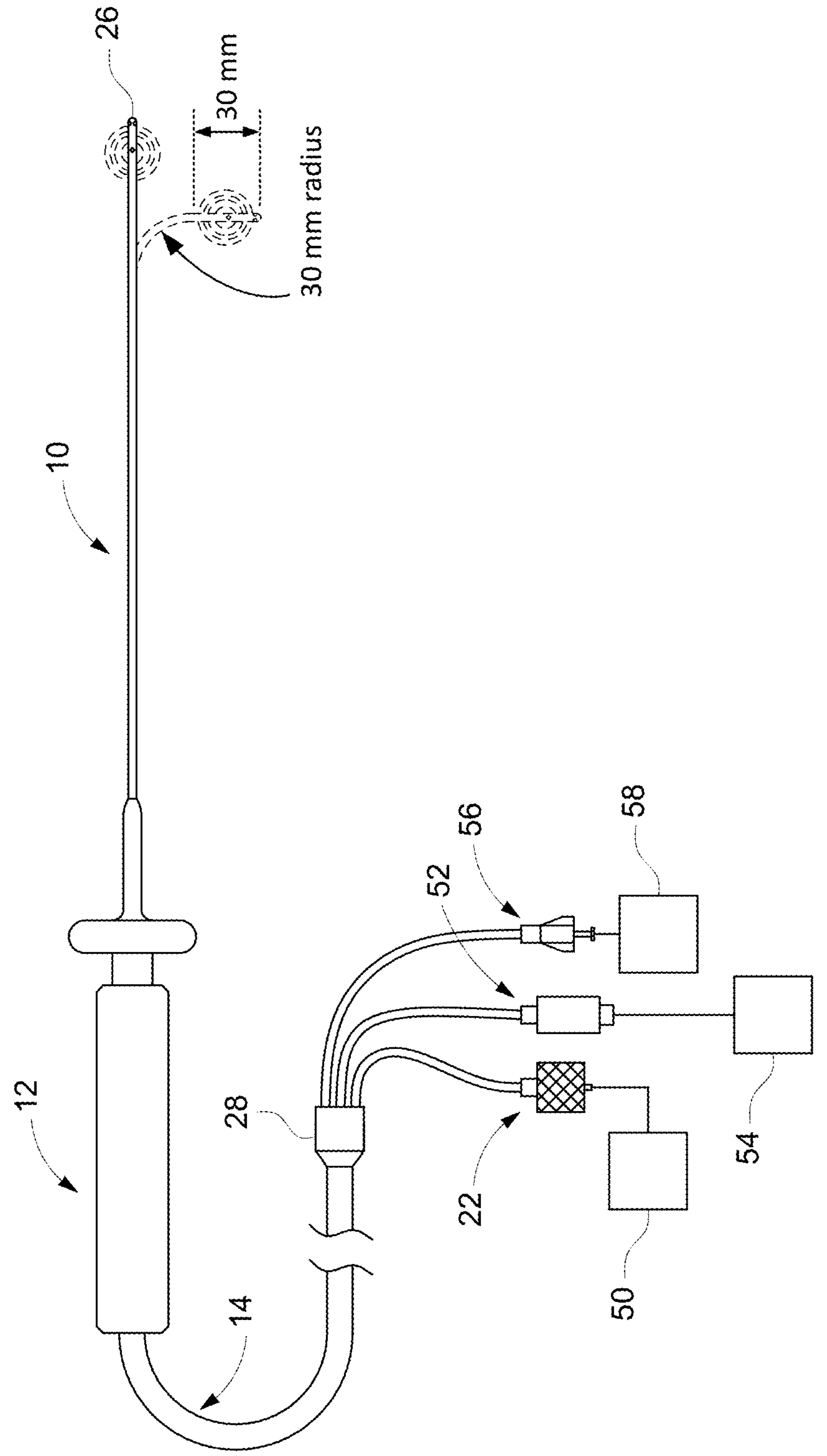
FIGS. 4, 5A-5C illustrate the device of FIG. 1 in a medical system and in use.

As shown in FIG. 4 catheter 10 connects at a handle 12 to a patient cable 14, at the proximal end 28 of which the microwave coaxial feedline 22 connects via a suitable connector 23 to a microwave generating source 50, electrical wires 40, 40', 40", 42 connect via a suitable connector 52 (such as one or more Redel 1P plug-in connectors), to an electrocardiogram processing/display module 54. ECG module 54 may include a signal processor and suitable monitors, displays and feedback means to assist use of the microwave catheter during an ablation procedure. Lumens 30, 30', 30" and 34, 34', 34" connect via a suitable connector 56 (such as one or more Luer locks) to a fluid control system 58, which includes suitable pump, control and flow measurement means, allowing selective adjustment of the flow parameters. Fluid control system 58 may also be used to introduce other fluids such as drugs into the fluid flow lumens for delivery to the catheter tip.

As will be understood, the catheter system may include other components and subsystems, such as a thermometry sensing system using a temperature sensing arrangement at the catheter distal end, to assist in monitoring operation during an ablation procedure. For this purpose, the catheter includes a thermocouple for temperature monitoring, positioned within around 1 mm of the distal end of the microwave feedline (ie. the end of the coaxial cable shield braid). This may involve use of an additional lumen running the length of the catheter system, e.g. connecting also through connector 52.

Along its length the catheter system can be seen to comprise two portions, a distal portion (catheter 10) between tip 26 and handle 12 and a proximal portion (including patient cable 14, in this example around 2 m in length) between handle 12 and proximal end 28.

In this example, catheter 10 is around 1100 mm in length, with a straight distal portion 30 mm in length (accommodating antenna and thermocouple) connecting via a flexible portion providing a minimum 30 mm bend radius, with flexion up to 180° (90° illustrated in dotted line). The distal anchor ring for the flexion mechanism is therefore away from the microwave field.

As previously noted, the catheter system may include additional design features as required and known in the art, such as features to assist in steering or otherwise guiding of the catheter tip or to augment tracking of the catheter tip.

Figure 5A:
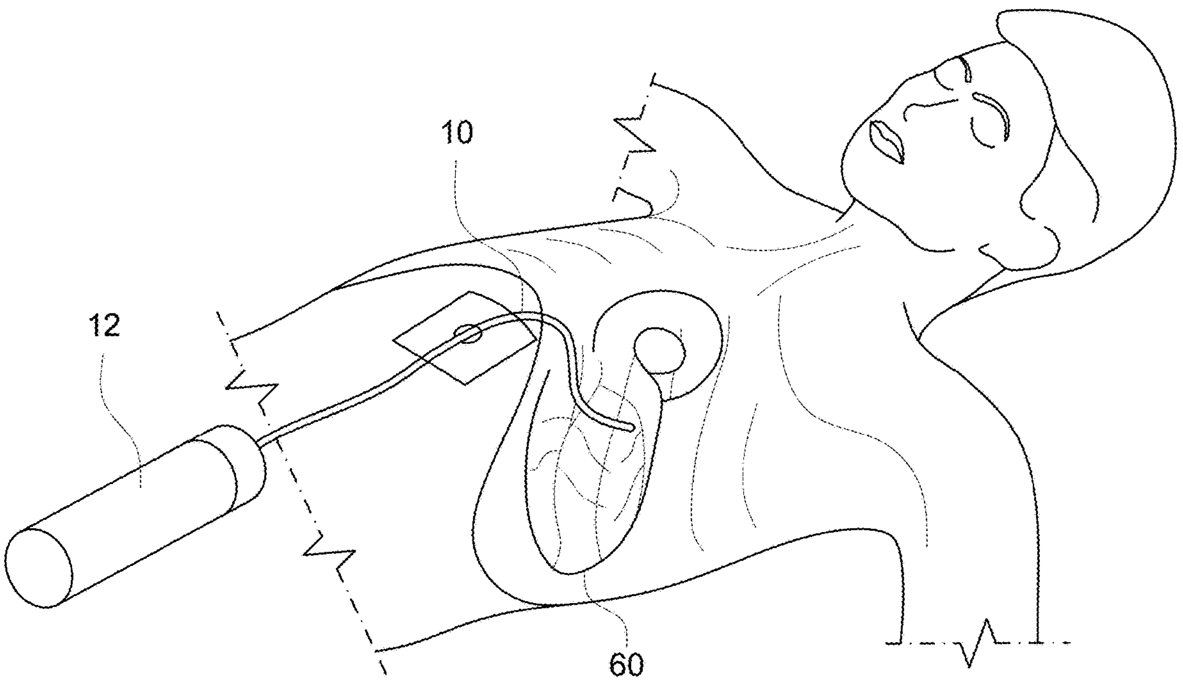
Figure 5B:
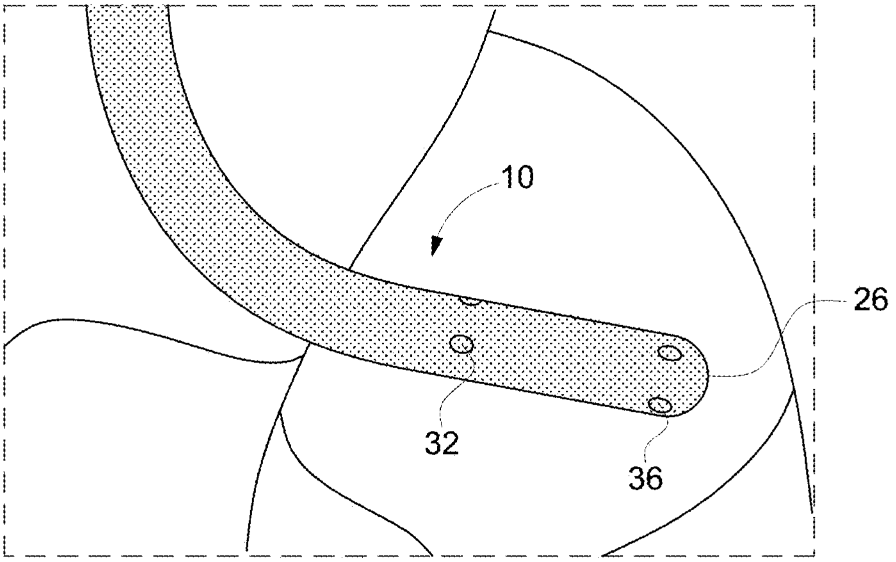
Figure 5C:
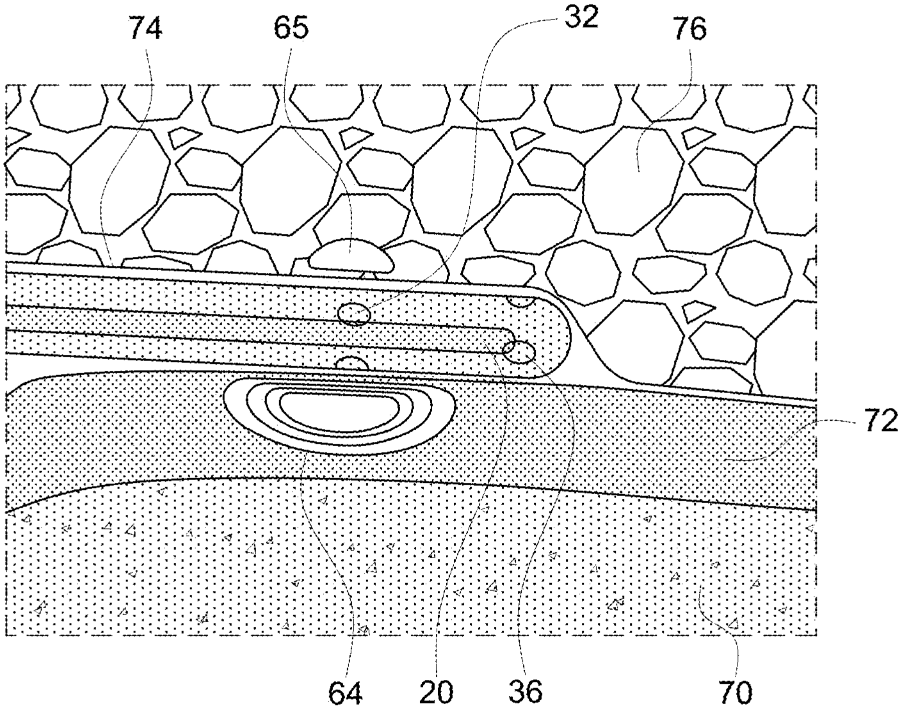

FIGS. 5A-5C illustrate use of the ablation catheter 10, in this case introduced into a ventricle of the heart 60 proximal to the location of a target area such as diseased or damaged tissue or a tissue region otherwise determined to be responsible for cardiac arrhythmia.

FIG. 5A shows the catheter deployed into the heart 60, FIG. 5B showing in more detail in plan view catheter 10 over the left summit (the portion of heart muscle between the left anterior descending artery and the circumflex, a source of arrhythmias).

FIG. 5C depicts the distal end of catheter 10 in place in the pericardial space, the tissues shown in section, namely the blood pool 70, the ventricular wall 72, the pericardium 74 and the lung field 76. Teflon-coated antenna 20 can be seen within the catheter sheath, as well as some of the irrigation/virtual electrode ports 32, 36.

In addition to ablation region 64, FIG. 5C also depicts a small lung heating region 65, discussed further below.

The catheter of the invention may be used endocardially or epicardially. For endocardial use a guiding sheath is generally inserted first, then catheter 10 is inserted through the guide. For epicardial use, a short, steerable sheath is generally inserted into the pericardial space and catheter 10 inserted through this guide. Because of the potential for tamponade and the absorption of microwave energy by the irrigation fluid, the pericardial fluid should be continually aspirated during the ablation procedure.

In the device described above, the catheter sheath in the distal portion is fabricated from a suitable biocompatible plastics material, namely Ensinger Plastics PEEK, which is resistant to microwaves and can be extruded or 3D printed into thinwall components. A variant not containing carbon fibre is preferred, to preclude possible interaction between carbon fibre components and the microwave field.

The device is preferably manufactured using a suitable extrusion technique, such as traditional coextrusion or combination extrusion.

Reinforcement of selected portions of the outer sheath may be provided. For example, around 450 mm of the proximal portion may comprise braided thinwall tubing.

The microwave feedline (coaxial cable 22) is provided by a suitable high power/low loss microwave cable. In tests, Molex Temp-Flex 086SC-2401 was used, which is a dual-braid/foil shield coax with a braid shield of 40 AWG silver-plated copper and a silver-plated copper core of 0.51 mm diameter. For enhanced flexibility, a multistrand silver-coated copper core is desirable. For the microwave antenna, the outer FEP jacket and braid of the feedline was removed over the selected tip length, and the foil coaxial layer encased with IRIDIUM heatshrink (Cobalt Polymers).

Conducting wires 40, 40', 40", 42 are provided by appropriate biocompatible material, such as titanium, platinum/iridium or stainless wire of around 0.2 mm diameter in a suitable insulation.

As discussed above, the septated nature of the catheter (and the insulating nature of the sheath material) provides the electrical separation between the different fluid columns, so to provide a high impedance circuit between electrodes and generate the virtual electrodes at orifices 32 (while allowing a common irrigant flow to supply all lumens with fluid). This arrangement thus provides a sensing electrode system independent and electrically isolated from the microwave antenna element.

However, as the skilled reader will appreciate, it is not necessary to continue the septation for the entire length of the catheter, for example the lumens may run for around 300 m from the catheter tip to an intermediate region (a length sufficient to provide sufficiently high impedance between the electrode ends of wires 40, 40', 40" and wire 42), with the remaining portion of the catheter (the proximal portion) provided by a single lumen defined by outer sheath 24, which single lumen provides the full fluid flow to feed all lumens 30, 30', 30", 34, 34', 34". For example, the lumens may combine at handle 12, which provides the intermediate region referred to above. Additionally, electrical wires 40, 40', 40" may interconnect to a single insulated wire running in parallel with wire 42 along the proximal portion of the catheter to electrocardiogram processing/display module 54. In this form, the intermediate region provides an electrical and fluid flow manifold.

The potential for a transcatheter system using microwave energy to form deep ventricular ablations in the epicardium has been demonstrated by the inventors by extensive in vitro and in vivo trials, which have established the safety of the procedure in the vicinity of coronary arteries. These trials have concluded that:

(1) Irrigated microwave ablation using the device can create lesions deeper and greater in dimension than possible using contact force irrigated radiofrequency ablation (the latest development in RF catheters);

(2) Deep microwave ablations can be formed through epicardial fat;

(3) Microwave ablations performed within 5 mm of coronary arteries can produce deep lesion without acute injury to the coronary artery (as would otherwise manifest by acute coronary vasospasm or occlusion).

(4) Collateral damage to the lung was found to be absent despite the large cardiac lesions, likely due to the significant difference in microwave permittivity of the inflated lung in comparison to the myocardium. In other words, the lung is not tuned to the microwave field, resulting in almost all of the microwave energy passing to the myocardium. FIG. 5C shows a small lung heating region 65, but the trials discussed below confirmed that this does not result in any damage to the lung.

Figure 6A:
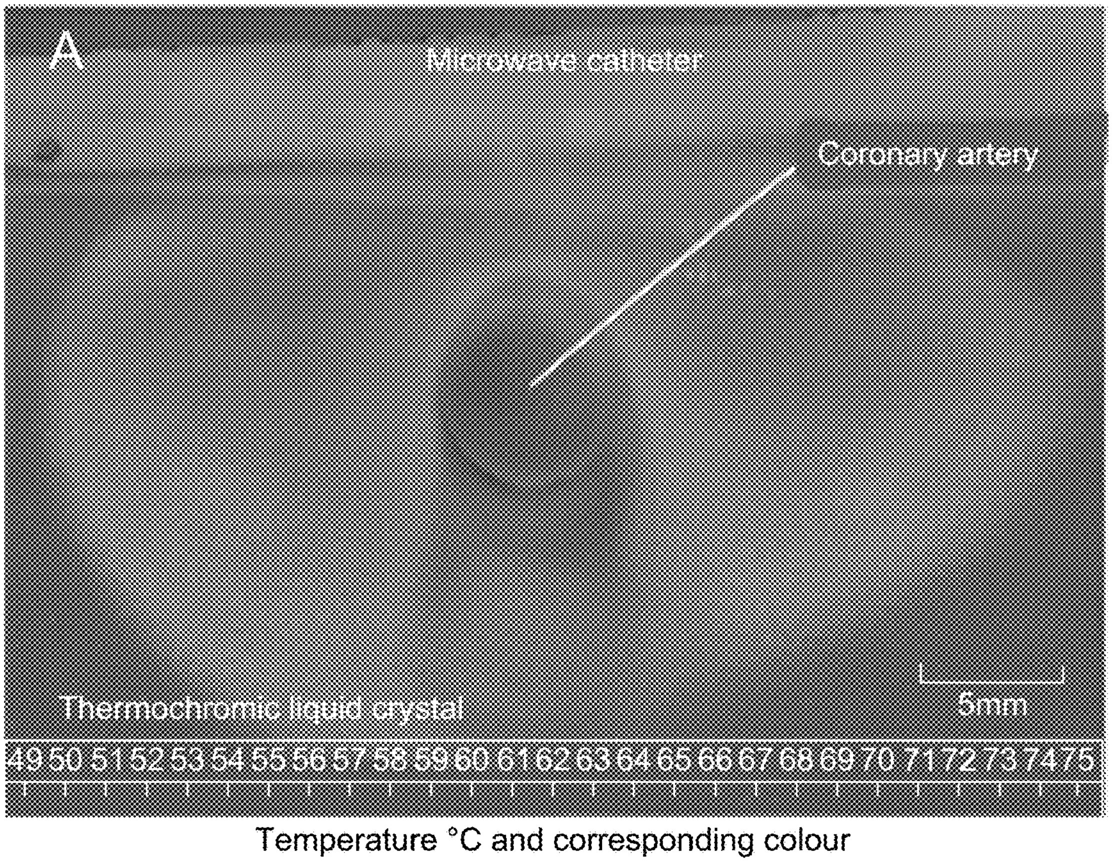
FIGS. 6A and 6B show results of trials of an embodiment of the invention.

In particular, in preliminary trials conducted by the inventors, an irrigated microwave ablation catheter in accordance with the invention (incorporating a full wavelength microwave antenna 20) was optimised in an in vitro model, consisting of a myocardial gel phantom embedded with a thermochromic liquid crystal sheet. FIG. 6A illustrates the position of the microwave catheter over the myocardial phantom with a coronary artery in section, perfused with 0.9% saline at physiological blood flow and at a temperature of 37° C. Sparing of the tissue adjacent to the coronary artery lumen is seen due to the cooling effect of arterial blood flow during deep microwave ablation directly over the coronary artery.

Epicardial ablation with the optimised catheter was then performed in sheep under general anaesthesia via standard percutaneous subxiphoid puncture access. The microwave catheter was positioned over the left ventricular summit, anterior interventricular groove and posterolateral left ventricle in proximity to coronary vessels. Ablations of 90-100 W at 20 mL/min for 4 min were delivered (with a 2450 MHz microwave field), with 12 ablations delivered in five sheep. Coronary angiography was performed after ablation.

From the post-operative analysis, the overlying epicardial fat thickness was measured at 2±3 mm. Microwave lesion depth was measured at 10±4 mm, width 18±10 mm, and length 29±8 mm. 10 out of the 12 ablations were found to be within 5 mm of a coronary artery, with a mean separation of 2.4±1.6 mm. The adjacent coronary arteries remained patent without focal narrowing angiographically. This is likely due to the cooling effect of coronary arterial blood flow on the arterial wall appreciated in the in vitro model.

Figure 6B:
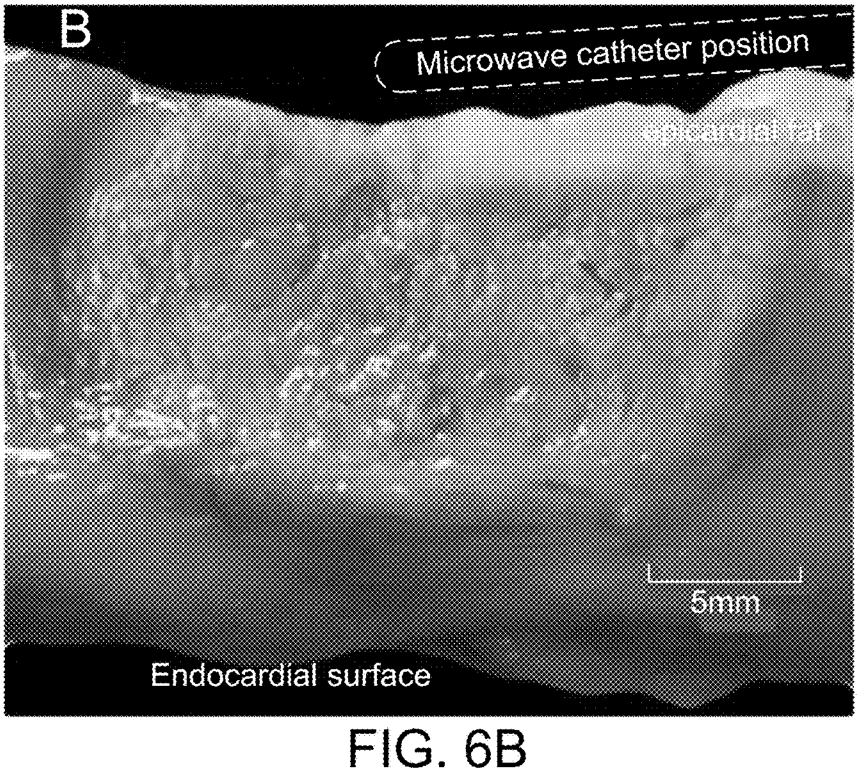

FIG. 6B shows a well demarcated and deep ablation lesion, despite the presence of significant overlying epicardial fat.

These preliminary trials also included lesion forming using different lengths of microwave antenna, which confirmed that the length of the lesions may be changed by varying the antenna length of the antenna.

These trials provide preliminary indication that transcatheter epicardial microwave ablation can be an effective and safe approach for ablation of ventricular tachycardia arising from the left ventricular summit or other regions previously inaccessible using conventional ablation approaches.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

What is claimed is:

1. An ablation lesion device for delivery of microwave energy to a selected region of tissue, the device comprising:

a microwave radiation antenna electrically connectible via a microwave feedline to an electrical microwave system, the microwave antenna configured to generate a microwave field able to ablate tissue in said selected region of tissue, the antenna positioned within an antenna-receiving portion of an elongated catheter for introduction via a blood vessel, the catheter configured to allow fluid flow along the catheter to exit into the blood vessel through one or more orifices in a catheter wall, the catheter comprising at least one lumen extending from a proximal portion to a distal portion, and an electrical sensing system including at least one metal electrode disposed within the at least one lumen at a location proximal to the antenna-receiving portion, the electrical sensing system being independent of the electrical microwave system, wherein the at least one lumen is configured to convey an electrically conductive irrigating fluid from the at least one metal electrode, along the lumen, past the antenna-receiving portion, and to at least one of the one or more orifices formed through the catheter wall, such that, in use, the fluid establishes an ionic conductivity bridge traversing said catheter antenna-receiving portion, and forms a virtual sensing electrode at said at least one of the one or more orifices, and wherein the antenna is configured to generate the microwave field external of said catheter, the microwave field having a field longitudinal extent which includes at least one of the one or more orifices.

2. An ablation lesion device according to claim 1, wherein at least one of the one or more orifices is positioned approximately centrally of said field longitudinal extent.

3. The ablation device according to claim 1, wherein:

the catheter further comprises a second lumen extending from the proximal portion to the distal portion and separated from the at least one lumen by an internal septum;

a second metal electrode is disposed within the second lumen at a location proximal to the antenna-receiving portion, the second metal electrode being electrically connectible to the electrical sensing system;

a second distal orifice is formed through the catheter wall in fluid communication with the second lumen, the second orifice being positioned distal to the second electrode and within a longitudinal extent of the microwave field generated by the antenna; and the second lumen is configured to convey an electrically conductive irrigating fluid from the second metal electrode, along the second lumen, past the antenna-receiving portion, and to the second distal orifice, such that, in use, the fluid establishes a second ionic conductivity bridge traversing the antenna-receiving portion and forms a second virtual sensing electrode at the second distal orifice.

4. The ablation device according to claim 3 wherein the first and second distal orifices are spaced apart along the length of the catheter and are fluidly and electrically isolated from each other within the distal portion of the catheter.

5. An ablation lesion device for delivery of microwave energy to a selected region of tissue, the device comprising:

a microwave radiation antenna electrically connectible via a microwave feedline to a source of microwave energy, the microwave antenna configured to generate a microwave field able to ablate tissue in said selected region of tissue;

a hollow catheter of elongated form extending from a proximal portion to a distal portion including a tip, the catheter having an outer wall to separate an inside and an outside of the catheter;

the catheter including an antenna-receiving part in said distal portion, the catheter configured to provide a passage for said microwave feedline to said antenna-receiving part;

the catheter having a septated form including a first and a second lumen arranged for fluid flow to the catheter distal portion;

an electrical sensing system independent of the source of microwave energy, the electrical sensing system comprising a first metal electrode positioned within the first lumen, and a second metal electrode positioned within the second lumen, wherein the first metal electrode and the second metal electrode are located in the catheter distal portion substantially proximal of said antenna-receiving part of the catheter;

the first lumen connecting with one or more first orifices formed through the catheter outer wall in said catheter distal portion to provide a first fluid outflow path from the first lumen to the outside of the catheter and the second lumen connecting with one or more second orifices formed through the catheter outer wall in said catheter distal portion to provide a second fluid outflow path from the second lumen to the outside of the catheter, wherein the one or more first orifices and the one or more second orifices are longitudinally spaced apart from each other, such that the first fluid outflow path and the second fluid outflow path are longitudinally separated from one another, and wherein the one or more first orifices and the one or more second orifices are fluidly and electrically isolated from each other within the catheter in the catheter distal portion;

wherein the microwave field generated by the antenna is external of said catheter and has a longitudinal extent such that the metal electrode is positioned outside the microwave field and one or both of the first and second orifices are positioned within the microwave field.

6. An ablation lesion device according to claim 5, wherein the catheter distal portion is provided with:

at least one tip orifice in the catheter wall at or close to the tip, and a lumen orifice in the catheter wall proximal of the catheter tip;

wherein said first lumen is connected to said antenna receiving part of the catheter to provide fluid thereto, the fluid exiting the catheter via said at least one tip orifice, said second lumen terminates in a fluid connection with the outside of the catheter via the lumen orifice, the at least one tip orifice and the lumen orifice are longitudinally separated along a substantial part of the antenna-receiving part of the catheter; and wherein the electrical sensing system includes a first insulated electrical wire arranged along said first lumen terminating in said first metal electrode and a second insulated electric wire arranged along said second lumen terminating in said second metal electrode.

7. An ablation lesion device according to claim 5 including multiple second lumens, each having a metal electrode and each having a lumen orifice, the lumen orifices substantially longitudinally coincident.

8. An ablation lesion device according to claim 7, wherein the lumen orifices are substantially longitudinally coincident with the region of maximum microwave field strength.

9. An ablation lesion device according to claim 5 including multiple first lumens, at least one provided with a metal electrode, all said first lumens connecting to the antenna-receiving part of the catheter.

10. An ablation lesion device according to claim 9 including multiple second lumens, each having a metal electrode and each having a lumen orifice, the lumen orifices substantially longitudinally coincident and wherein at least three of said first lumens and at least three of said second lumens are arranged in an alternating disposition within the catheter in the volume between said microwave feedline and said catheter wall.

11. An ablation lesion device according to claim 5, wherein the first and second lumens are connected for common fluid flow in said catheter proximal of said distal portion.

* * * * *